United States Patent [19]

Kamentsky et al.

[11] Patent Number: 5,793,969
[45] Date of Patent: Aug. 11, 1998

[54] NETWORK REVIEW AND ANALYSIS OF COMPUTER ENCODED SLIDES

[75] Inventors: Louis A. Kamentsky, Boston; Mark Weissman, Wayland; Lee D. Kamentsky, Arlington; Russell Gershman, Middleboro; B. Martin Pomeroy, Framingham, all of Mass.

[73] Assignee: NeoPath, Inc., Redmond, Wash.

[21] Appl. No.: 585,183

[22] Filed: Jan. 11, 1996

Related U.S. Application Data

[63] Continuation-in-part of Ser. No. 89,243, Jul. 9, 1993, Pat. No. 5,587,833.

[51] Int. Cl.$^6$ .................... H04L 12/00; G06K 9/00; G06F 13/00
[52] U.S. Cl. .................... 395/200.43; 395/200.47; 395/200.48; 395/200.49; 364/579; 364/580; 364/550; 364/552; 364/134; 382/128; 356/39; 359/363; 359/368; 359/391
[58] Field of Search .................... 364/514 A, 514 R, 364/579, 580, 138, 134, 496–498, 550, 525, 552; 382/128, 133; 356/39, 40, 346; 359/363, 368, 391, 398, 393; 395/200.43, 200.47–200.49

[56] References Cited

U.S. PATENT DOCUMENTS

| | | | |
|---|---|---|---|
| 4,888,714 | 12/1989 | Dingle | 364/525 |
| 5,008,185 | 4/1991 | Bacus | 435/7.23 |
| 5,072,382 | 12/1991 | Kamentsky | 382/133 |
| 5,216,596 | 6/1993 | Weinstein | 128/665 |
| 5,235,522 | 8/1993 | Bacus | 364/497 |
| 5,297,034 | 3/1994 | Weinstein | 382/128 |
| 5,321,520 | 6/1994 | Inga et al. | 358/403 |
| 5,333,207 | 7/1994 | Rutenberg | 382/133 |
| 5,367,401 | 11/1994 | Saulietis | 359/398 |
| 5,384,643 | 1/1995 | Inga et al. | 358/403 |
| 5,428,690 | 6/1995 | Bacus et al. | 382/128 |
| 5,526,258 | 6/1996 | Bacus | 382/129 |
| 5,619,428 | 4/1997 | Lee et al. | 364/551.01 |

*Primary Examiner*—Emanuel Todd Voeltz
*Assistant Examiner*—Tuan Q. Dam
*Attorney, Agent, or Firm*—Hans I. Sun; Emil Moffa

[57] ABSTRACT

A network system for review and analysis of computer encoded microscope slides and specimens which were originally computer encoded from a microscope (attached via an encoder device to a local computer site), during an initial examination. The encoding includes parameters of viewing locations and events of interest on the slide, with such information being stored on a networked file server. The encoding also includes information regarding the manner in which the initial examination was conducted, for quality control purposes. The computer encoded information is retrievable at all remote locations of the network (either local or connected via modem) for supervisor review or for pathologist analysis. The network is further constituted by microscope sites having similar computer encoding devices attached thereto, which function, in this aspect, as computer terminals of the network. For enhanced analysis, the computer terminals have direct access to patient background information, e.g., such as from an HIS (hospital information system) for simultaneous slide analysis review in relation to the medical history of the patient. For diagnostic support, the computer terminals are networked with an on-line library of cell type images for comparison with the slide being examined. Slide diagnosis is either directly with the original slide on the microscope or with a scanned image of the slide stored in the network server or CD-ROM and retrieved on the computer terminal. The microscope is optionally motor driven, with computer control, to re-scan slides or slide images only at designated sites.

28 Claims, 4 Drawing Sheets

Fig. 2

NETWORK REVIEW AND ANALYSIS OF COMPUTER ENCODED SLIDES

This a continuation-in-part of application Ser. No. 08/089.243, filed Jul. 9, 1993 now U.S. Pat. No. 5,587,833.

FIELD OF THE INVENTION

This invention relates to computerized review of computer encoded microscope slides after examination of specimens thereon, and particularly with respect to multi-site examination thereof.

BACKGROUND OF THE INVENTION

Various devices exist for use in the review of previously examined microscope slides for facilitated re-examination, as a quality control, and as a gauge with respect to the degree of reliability of initial slide examination test results.

One of such devices and methods of re-examination is disclosed in the parent of the present application wherein an encoder device is described which retrievably provides computer encoding of positions of the slide which were examined initially. Movement of the microscope stage on which the slide is positioned correspondingly records position location on a computer generatable image of a slide. As a result, retrieval of the computer encoded examination provides a slide image having markings thereon which indicates areas of the slide which were examined (and the absence of which indicates areas which were not examined). Co-pending application, Ser. No. 08/491,414, filed Jun. 16, 1995 now U.S. Pat. No. 5,602,679, provides a further enhancement for determining which areas were examined, for how long, whether there was overlapping of viewing, the percentage of the slide area screened and the like. In such co-pending application, a grayscale display is used to indicate relative dwell time at each location (or pixel of the computer representative image), whereby during rapid screening, the central area of a moving circular cursor that sweeps out a track on the screen, is darker than the edges of the field of view. In addition, as a screener overlaps the column or row on the next pass, the time spent on the overlapping edges is added, and the edges darken to indicate additional inspection time. Based on variations in the grayscale, the device further provided the percentage of overlapping fields as a useful measure of screening performance, which screeners and screening reviewers were able to use to refine performance, i.e., too little overlap can lead to false negative findings, while too much overlap indicates inefficient performance. A supervisor is thereby provided with a rational and efficient quality control method for choosing which specimens to review for teaching and quality control purposes.

Use of the internal computer clock further enabled placement of the markings in a time dependent manner such that a determination could be made with respect to the examination dwell time in the examined areas.

As a further feature, in the parent application, selected marked areas of specified locations in the slide specimens were able to be marked in computer memory (visually or with audio) to indicate whether such areas on the actual slide are of particular interest and if so, with pre-determined coding, to additionally mark such slide viewing areas. As a result, the areas having such additional interest markings are thereby able to be re-examined with greater ease in location and re-location.

Other systems extant, operate with actual imaging of slide contents, such as with video cameras and the like, coupled with slide location mapping for retrieval location of specific areas of interest. Video images are digitized for facility in computer storage and retrieval purposes. However, all of the slide reexamination systems and procedures have been confined to a single site, and review of the original slide or image thereof, and, in some systems, with a computerized review of the encoded procedures utilized in obtaining the initial results.

SUMMARY OF THE INVENTION

It is accordingly an object of the present invention to provide a means for multiple simultaneous review of encoded information obtained from the slide analysis procedures of a microscope slide, including the manner in which the slide analysis was conducted and optionally including stored images of the slide.

It is a further object of the present invention to provide such means for review at two or more networked remotely located microscope sites linked to computer encoder-terminals.

It is yet another object of the present invention to permit the multiple review of flagged slide specimen view sites at two or more remotely located terminal sites.

It is still yet another object of the present invention to provide network capability at the terminal sites, for correlating slide information together with patient history and/or together with comparative observation information to resolve possible ambiguities in interpretation.

It is another further object of the present invention to provide automatic location and review of the flagged slide specimen view sites.

It is a still further object of the present invention to provide report generation in HIS (health information systems) systems for full patient records.

These and other objects, features and advantages of the present invention will become evident from the following discussion and drawings in which:

BRIEF DESCRIPTION OF THE DRAWINGS

FIG. 2 is a window field showing slide review, patient history and information and selected recorded images of the slide;

DETAILED DESCRIPTION OF THE INVENTION

Figure 1:
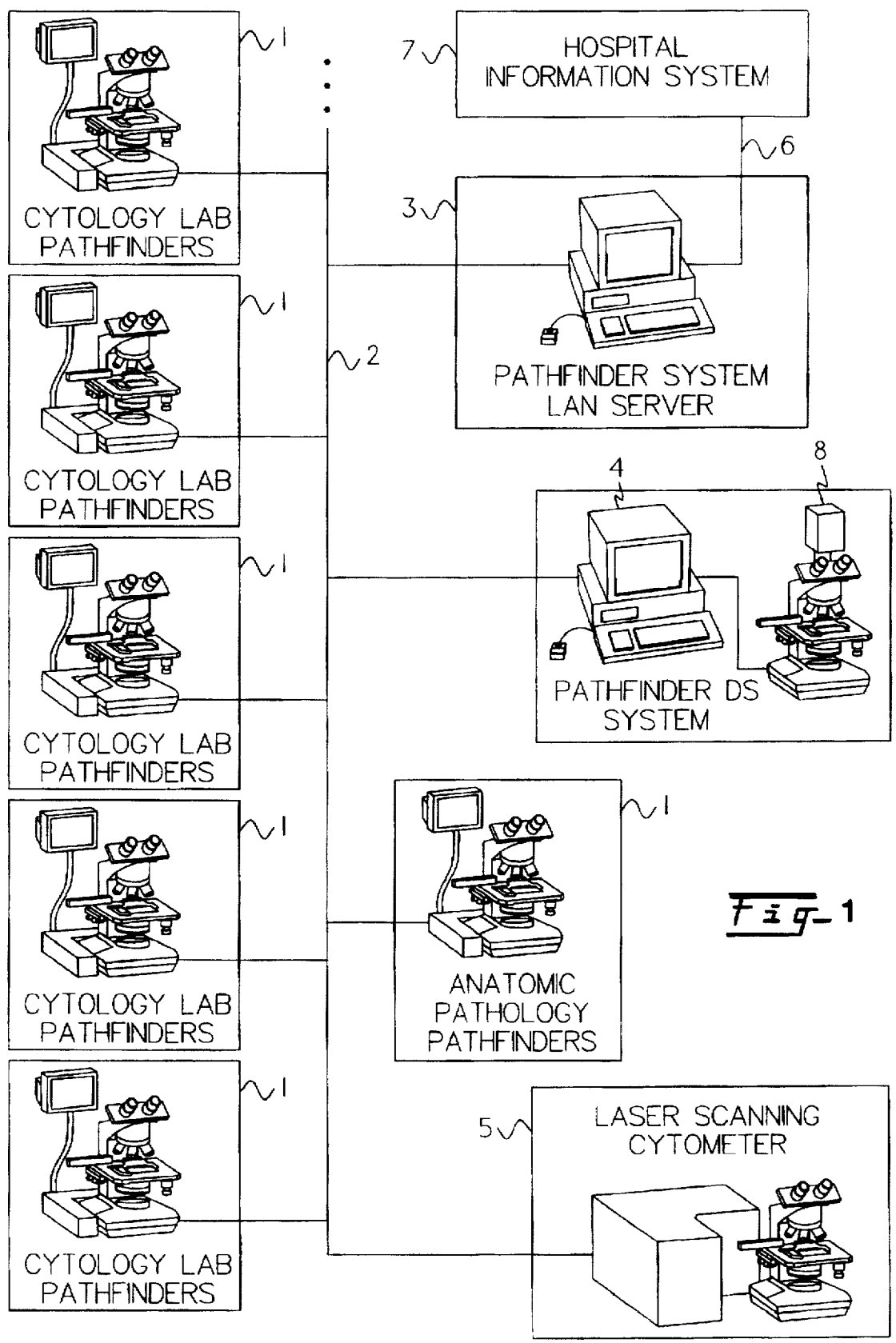
FIG. 1 schematically depicts a networked system of microscope sites, with linked computer encoders; HIS network file server; data supply system; and cytometer station.

Generally the present invention comprises method for network reviewing of a specimen slide and the manner in which a prior microscope examination of the specimen slide was conducted and the networked system. The method relates to selected details of the specimen of the specimen slide and the manner of examination thereof which were computer encoded, during prior scanning examination thereof. The original examination having been conducted with a microscope having viewing means and a moving slide stage, on which the specimen slide was mounted, wherein encoding of the details of the specimen and the manner of examination thereof was effected by:

a) operatively linking computer means, with correlation movement sensor means, to the movable slide stage of the microscope, to correlatively record movement of the slide stage in an x-y direction plane in which the slide stage is movable;

b) recording movement and various locations of the slide stage during the microscope examination of the specimen slide, at various locations on the specimen slide, by means of the linked computer means, pursuant to programmed instructions, into computer storage means; and wherein the computer means, pursuant to additional programmed instructions automatically records, into the computer storage means, information relating to the stored various locations and the manner in which the examination was conducted. The network reviewing method comprises the step of causing the computer storage means to be independently accessible by at least two separate microscope stations in a network, each of the stations comprising a microscope and computer means, with each of the microscope stations being separately individually linked to at least one computer means capable of recalling the stored movements and location information from the storage means for review at a location remote from the microscope used in the original examination.

In a preferred embodiment the present invention comprises a method for network reviewing of a specimen slide and the manner in which a prior microscope examination of the specimen slide was conducted, wherein selected details of the specimen of the specimen slide and the manner of examination thereof were computer encoded, during prior scanning examination thereof with a microscope having viewing means and a moving slide stage, on which the specimen slide was mounted, wherein encoding of the details of the specimen and the manner of examination thereof was effected by:

a) operatively linking computer means, with correlation movement sensor means, to the movable slide stage of the microscope, to correlatively record movement of the slide stage in an x-y direction plane in which the slide stage is movable;

b) recording movement and various locations of the slide stage during the microscope examination of the specimen slide, at various locations on the specimen slide, by means of the linked computer means, pursuant to programmed instructions, into computer storage means; and wherein the computer means, pursuant to additional programmed instructions automatically records, into the computer storage means, at the stored various locations, pre-determined indicia, with said indicia correlating to the microscope viewing area location on the specimen, and wherein said indicia, correlating to viewing area locations of interest were marked and recorded with a distinguishing marking for subsequent review recognition; said network reviewing method comprising the steps of:

a) causing the computer storage means to be independently accessible by at least two separate microscope stations in a network, each of said stations comprising a microscope and computer viewing means, with each of said microscope stations being separately individually linked to at least one computer means capable of recalling said stored movements, locations and indicia from the storage means for review on the computer viewing means:

b) recalling, at one or more of said microscope stations, from said computer storage means, a computer generated image of a slide with said indicia thereon, onto the viewing means of the respective microscope station, for review of the manner in which a prior microscope examination of the specimen slide was conducted; and i) placing the specimen slide on the movable slide stage of the microscope, at the respective microscope station, with the microscope thereat being further operatively linked with the computer means, by correlation movement sensor means;

ii) moving the stage, with concomitant specimen slide movement, with correlation of each subsequent microscope viewing area with indicia on the computer generated image, by indicator means, whereby correlated indicia having a distinguishing marking thereon is directly viewable with the microscope.

With reference to the parent application, the present invention also comprises a method for network reviewing of a specimen slide and the manner in which a prior microscope examination of the specimen slide was conducted, wherein selected details of the specimen of the specimen slide and the manner of examination thereof were computer encoded, during prior scanning examination thereof with a microscope having viewing means and a moving slide stage, on which the specimen slide was mounted, wherein encoding of the details of the specimen and the manner of examination thereof was effected by:

a) operatively linking computer means, with correlation movement sensor means, to the movable slide stage of the microscope, to correlatively record movement of the slide stage in an x-y direction plane in which the slide stage is movable;

b) recording movement and various locations of the slide stage during the microscope examination of the specimen slide, at various locations on the specimen slide, by means of the linked computer means, pursuant to programmed instructions, into computer storage means; and wherein the computer means, pursuant to additional programmed instructions and an internal clock of the computer means, automatically recorded, into the computer storage means, at the stored various locations, pre-determined indicia at predetermined time intervals, determined by said internal clock, with said indicia correlating to the microscope viewing area location on the specimen, at the predetermined time intervals; and wherein said indicia, correlating to viewing area locations of interest were optionally marked and recorded with a distinguishing marking for subsequent review recognition; said network reviewing method comprising the steps of:

a) causing the computer storage means to be independently accessible by at least two separate microscope stations in a network, each of said stations comprising a microscope and computer viewing means, with each of said microscope stations being separately individually linked to at least one computer means capable of recalling said stored movements, locations and indicia from the storage means for review on the computer viewing means:

b) recalling, at one or more of said microscope stations, from said computer storage means, a computer generated image of a slide with said indicia thereon, onto the viewing means of the respective microscope station, for review of the manner in which a prior microscope examination of the specimen slide was conducted; and if indicia correlating to sites of interest have been marked with a distinguishing marking:

i) placing the specimen slide on the movable slide stage of the microscope, at the respective microscope station, with the microscope thereat being further operatively linked with the computer means, by correlation movement sensor means;

ii) moving the stage, with concomitant specimen slide movement, with correlation of each subsequent microscope viewing area with indicia on the computer generated image, by indicator means, whereby correlated indicia having a distinguishing marking thereon is directly viewable with the microscope.

The present invention includes a network system for review and analysis of computer encoded microscope slides and specimens which were originally computer encoded from a microscope (attached via an encoder device to a local computer site), during an initial examination with an encoding system. The encoding includes parameters of viewing locations and events of interest on the slide, with such information being stored on a networked file server. The encoding also includes information regarding the manner in which the initial examination was conducted, for quality control purposes. The computer encoded information is retrievable at all remote locations of the network (either local or connected via modem) for supervisor review or for pathologist analysis. The network is further constituted by microscope sites having similar computer encoding devices attached thereto, which function, in this aspect, as computer terminals of the network. For enhanced analysis, the computer terminals have direct access to patient background information, e.g., such as from an HIS (hospital information system) for simultaneous slide analysis review in relation to the medical history of the patient. For diagnostic support, the computer terminals are networked with an on-line library of cell type images for comparison with the slide being examined. Slide diagnosis is either directly with the original slide on the microscope or with a scanned digital image of the slide stored in the network server or CD-ROM and retrieved on the computer terminal. The microscope is optionally motor driven, with computer control, to relocate slide images only at designated sites.

The following discussion relates to the various required and optional examination steps involved in the present invention:

1) Specimen Selection

Providing means to communicate encoding system data is not useful unless means are provided for selecting microscopic slides that require review by another individual. Means are accordingly provided for selecting appropriate computer files generated by each of multiple encoding systems to create new files for supervisor' or pathologist' encoding systems who review prior slide examinations. A user interface to perform this task is therefore an integral part of the encoding system.

2) Demographics

Diagnostic judgments are based not only on the appearance of specific cells viewed microscopically, but on patient demographics and prior clinical history. Diagnostic decisions can be aided if the encoding system provides medical information from a Hospital Information System (HIS) to support these decisions. This affords an important additional benefit to the Hospital Information System in that not only is patient information available for use by the encoding system user, but that the encoding system itself can provide a computer terminal for entry of patient data, derived from observations of the slide, directly into the Hospital Information System for immediate use by others. Such data can be numeric data from a differential cell count of a blood smear, urine specimen, microbiology specimen or body fluid cytospin or it can be a cytologic or anatomic pathologic diagnosis text report.

3) Diagnostic Decision Support

Diagnostic decisions, after observation of potentially pathologic cells on a specimen slide, are sometimes ambiguous even utilizing prior patient information. The pathologist will often review images of cells by looking at other microscope slides, images in textbooks and images on 35 mm film slides in order to compare them with the cells of the patient specimen to reach a diagnosis. In accordance with the present invention the encoding system, is capable of supporting diagnostic decisions by retrieving images from files and displaying them with the specimen cell images digitized by means of a video camera. In addition, patient demographics and prior data entries are retrievable in the network, to suggest what should be observed on the microscope slide and what diagnoses may be possible.

4) Report Generation

Anatomic pathology or cytology diagnoses must be reported and a permanent record must be generated in the Hospital Information System. This report should include encoding system data such as maps of the location and types of unusual cells as well as images of some of these cells digitized by means of a video camera. The encoding system data permits better document the efficacy of the laboratory as well as providing images and cell locations for use during comparisons with cells from subsequent examinations, whereby it is possible to follow and document disease progression.

5) Scanning Instruments

Instruments for scanning specimens of cells on microscope slides, using a laser or a video camera, identify specific cells by their constituents, their genotype or phenotype, or their pathology. This type of instrument is used in medical and research laboratories, with some of these instruments being capable of recording the position on the microscope slide of each cell measured. These devices are interfaced, in accordance with a preferred embodiment of the present invention, to an encoding system in order:

1) to annotate cells or areas of a slide containing a specific type of cell (such as a cancer area) so that only these cells or the specific area will be scanned by the instrument; or 2) after slides are scanned by the instrument, the encoding system can be used to locate and visually review, report on and include images of specific cells based on properties found by the instrument.

6) Automatic Relocation

In order to minimize time and effort of pathologists, in a preferred embodiment, the encoding system is comprised of a motorized stage. As a result, cell relocation of annotated slide areas is mechanized.

DETAILED DESCRIPTION OF THE DRAWINGS AND THE PREFERRED EMBODIMENTS

With reference to the drawings, FIG. 1 is a diagram of the preferred embodiment of the networked encoder system. One or more encoders 1, each consisting of a microscope equipped with stage position encoders, are interfaced with a microprocessor, a display screen and a keyboard. These encoders are used by laboratory personnel to screen and review microscope slides as described in the parent of this application. In accordance with the present invention each encoder contains an additional circuit, such as a MAX491 transmitter and receiver chip connected directly to the microprocessor's UART input/output lines, which enables communication via asynchronous line protocol using RS485 line drivers. The receiver and transmitter chip are connected to a twisted pair of wires 2 running throughout a laboratory area having multiple encoders, with each encoder being connected to the wires, i.e., "Daisy Chained". The wires are connected to PC CPU 3, which serves as the encoder system LAN server. One or more encoder DS Systems 4 and scanning instruments 5 may be connected to the network, provided that each uses a computer containing a network interface card, e.g., FASTCOM serial adapter board (Industrial Computer Source).

Communication between the server and all encoders and other devices connected on the network wires 2 is effected by means of appropriate software with communication being in forms of packets having a defined structure. This structure contains the address of a device, a command or status byte, error control information and optionally a data field. Each communication on the network consists of the server sending a single packet to a particular device, the first byte of which is one device's address. The devices determine if the address corresponds to their address and only the one device with the correct address will receive the remainder of the packet. It will check for errors and respond with a single packet sent to the server. The server continually polls all devices to determine if any need to either send data to the server or to receive data from it.

The server 3 of FIG. 1 is a standard PC computer operating the encoder System network using the Microsoft Windows™ (3.1 or 95), NT or other similar operating system. Any commercially available Ethernet card can be inserted into a spare buss circuit board slot in the computer. The Ethernet card is in turn connected by wire 6 to any other computer with an operating system compatible with the Microsoft Windows operating system on the server. The encoder software utilizes an ODBC standard database structure to store and retrieve specimen data and patient demographics. Medical organizations are adopting standards such as HL7 to provide standard names of specific fields to be used in data files. By combining these standards it is possible for computer database programs of different systems to communicate with each other to either find or send specific items of data.

With a Hospital Information System link, encoder users are able to retrieve specimen lists entered at an accession desk and use these to select the current specimen being examined as well as being able to call up and display patient demographics and history to help reach decisions. Optionally results may be directly read into the Hospital Information System, with the encoders can serving as data terminals for microscope users to enter data in the Hospital Information System.

As shown in FIG. 1, the encoder DS sub System comprises a PC computer 4 configured with a CD-ROM drive, encoder software, Diagnosis Decision Support software (DDSS), and interface cards connecting the PC to a microscope equipped with encoder stage position encoders and a CCD video camera 8.

Figure 4:
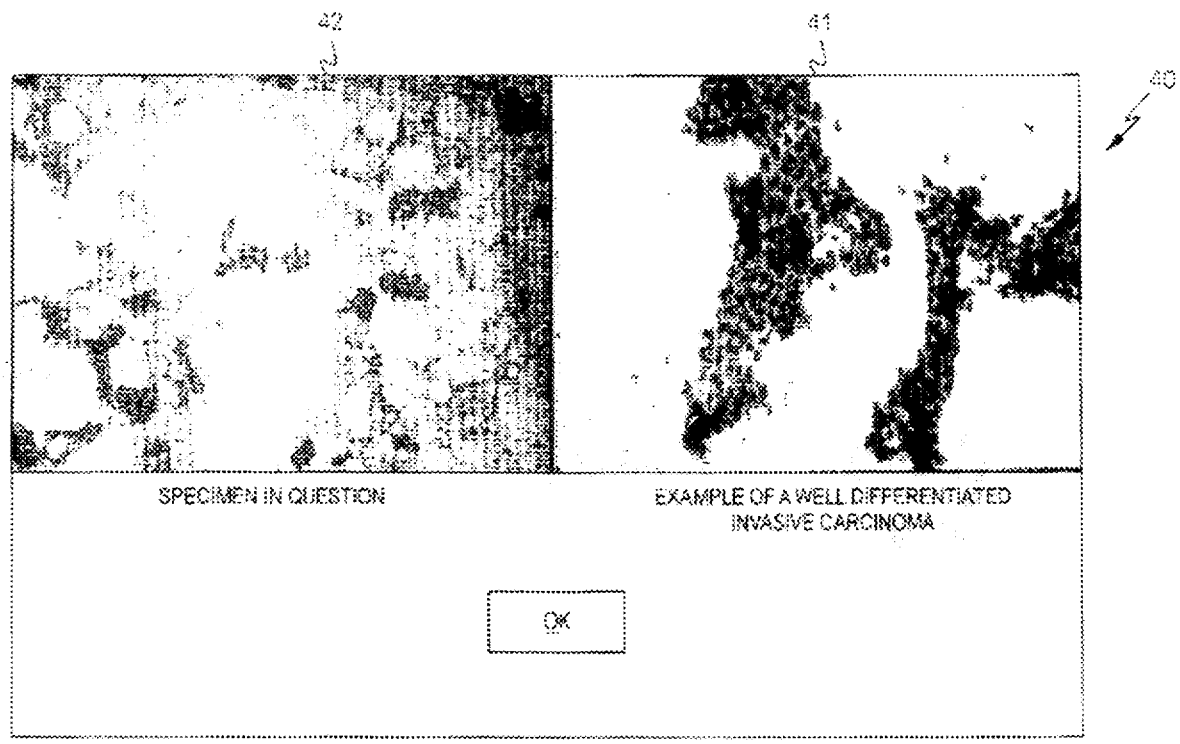
FIG. 4 is a comparative window between patient slide and library recalled slide image.

The DDSS component comprises 1) a database of microphotographic examples of proven cases at scanning and high-power magnifications. (FIG. 4, depicts a window 40 of comparative display of a proven case 41 and the current slide image 42) 2) algorithms to help direct the microscopic examination of the specimen. 3) expert commentary on differential diagnoses with recommendations for further diagnostic pathology testing (immunohistochemistry, special stains, etc.), 4) regularly updated medical references, and 5) software utilities enabling pathologists to capture, archive, and retrieve their own images/cases. These components are preferably on CD-ROM disks.

The encoder DS System provides practice guidelines for pathologists in the diagnosis of difficult cases; and facilitates diagnostic consistency in rapidly evolving areas of cytopathology specimen procurement such as fine needle aspiration. Quality assurance efforts are thereby enhanced by providing more standardized criteria and algorithms for specimen diagnosis; and it provides upto-date knowledge about the criteria used by experts to support specific diagnoses to thereby avoid common pitfalls.

In practice, the pathologist places the specimen on a network linked microscope with encoder and uses the PC to access demographic information from the Hospital Information System. The DDSS program then generates algorithms to help direct the microscopic examination of the specimen. The precise location of significant features of the specimen identified by a pathologist is determined by the encoder with programmed instruction and saved for future relocation. Additionally, images of the specimen captured by the CCD camera, are compared alongside images of proven cases in the DDSS database. These specimen images may also be incorporated into a pathologist's report and saved into his or her own database and used for future reference. DDSS algorithms identify a "most likely" diagnosis based on the pathologist's input into the diagnostic algorithm, the program then is able to make recommendations for further diagnostic pathology testing and to provide up-to-date medical references.

Figure 2:
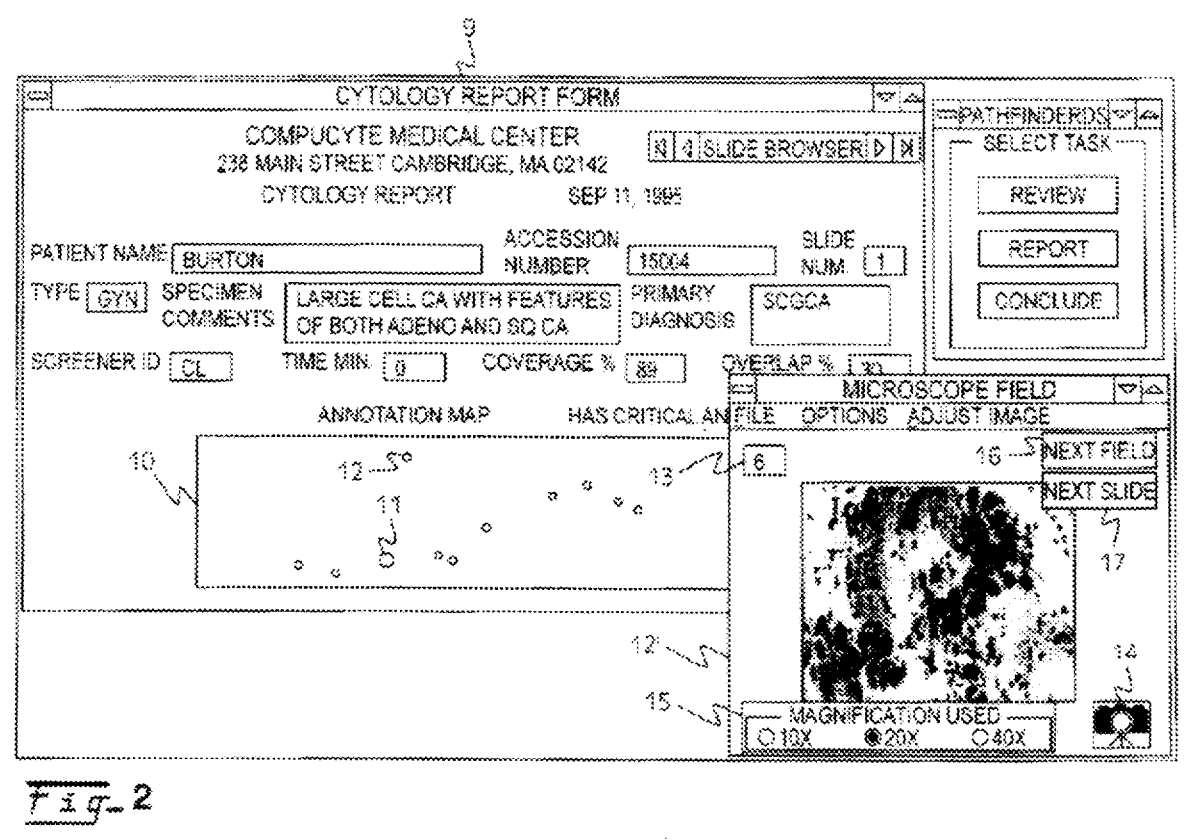

As shown in FIG. 1 a PC computer 4 is interfaced with a microscope stage encoder. Encoder interface boards are commercially available (e.g., Technology80, Inc.). With appropriate software a PC computer, operating under Microsoft Windows is able to perform encoder functions using encoder generated data or data from the encoder system network 2. The PC computer based encoder (encoder DS) 4 is connected to a microscope equipped with a CCD video camera 8 arranged so that a microscopic field can be viewed or imaged into the camera. The video camera in turn is connected to a commercially available frame grabber board in the PC computer (e.g., from Hauppauge Computer Works, Inc.). Appropriate software provides for the additional functions of generating a report, form 9 of FIG. 2, which can be electronically stored or printed. This form contains encoder data including the annotation map 10. A reviewer is then able to find cells on a slide by moving the microscope stage until a visible cursor 11 on the annotation map is coincident with an annotation mark such as 12. Annotations for various types are differentiated by different colors, not visible in the black and white rendering of FIG. 2. When the cursor is within a preset distance from an annotation, the image of the microscope field is made to appear in a window 12' on the computer monitor and the annotation number in the area 13. To do this, software was written to utilize the frame capture capability of the frame grabber board and the manufacturer's display software. Superimposed on the image is a button 14 which can be pushed using the computer's mouse to store the image in computer memory. The user is able to indicate the microscope objective used by clicking one of the buttons on the panel 15 with the mouse. The user can also store multiple images of any field at different focuses of the microscope at any of the magnifications. All such images are stored and appropriately indexed with appropriate software instruction. In a preferred embodiment the microscope is equipped with a mechanism to automatically move the focus position as images are being captured and stored. Review and image capture is then repeated for each annotation by clicking the Next Field button 16 or a different slide can be reviewed by clicking the Next Slide button 17. It is possible to generate computer records not only with encoder data, but records containing images of the cells causing the annotations. It is also possible to include database fields consisting of voice records for vocally commenting on cells or the specimen. This can be implemented with the addition of a commercially available PC computer sound card and software to place recorded files into the database.

Figure 3:
FIG. 3 is a report window field.

A further Reporting Window 18 is shown in FIG. 3. The patient's accession number is selected through icon 19 or entered in box 20, at which time the list of annotations found on the slide appear in box 21. Upon selecting an annotation number, all of the images of that slide field are transferred from disk storage to RAM storage for instantaneous viewing. The user can then, with a mouse, select a magnification using the buttons in the field 22 and a focus using the set of two up and down focus buttons 23 to call up and display in the Window 24 the appropriate image of the annotated microscope field. Window 18 also provides Text Boxes 25 for typing in the cytology diagnosis and 26 for later typing in the results of any histology done on the patient. Concurrence of these two text reports may be given a numerical value, with this value being stored along with the text and images for each slide for use in laboratory quality control.

There are at least four types of instruments, hematology analyzers, PAP smear analyzers, image analyzers and the CompuCyte LSC™ (trademark) laser scanning cytomer, in which microscope slides are scanned, the data from scans is processed, cells are digitally located and isolated and the cells are characterized, based on the scan data. One or more of the instruments can be interfaced with at least one of the microscope stations on network in accordance with the present invention.

With each instrument, the cells can be classified and their type and location on the slide recorded in a digital medium. The LSC (5 of FIG. 1) is an example of a scanning instrument which can be connected to the encoder system network 2 by inserting a FASTCOM network card in the LSC's PC computer. The LSC can scan slides stained with fluorescent dyes to measure the constituents and morphology of cells on the slide and generate a computer database file containing a set of constituent values, morphology values and slide position values for every cell found by it on the slide. The position coordinates of the LSC can be calibrated to the same positional frame as the encoder system devices using a calibration slide, as described in the copending application.

Slides to be examined with the LSC are often made by touching a surgically resected tissue to a slide or they may use tissue sections fixed to the slide. They therefore may contain normal as well as pathologic areas corresponding to normal and abnormal areas of the original tissue. It is advantageous to indicate to the LSC, by visual observation, the type of cells in each area of the slide, or to mark specific cells prior to scanning the slide. For example, a specimen may contain many more normal cells than cancer cells and if all cells were scanned, the resulting statistics may hide the characteristics of the cancer cells. If only the cancer area were scanned, the resulting data is more useful in determining treatment of the cancer. Accordingly, the slide is placed on an encoder DS, connected to a phase or fluorescent microscope. Cells on the slide are viewed and the stage is moved to specific areas of interest. Corners of the slide area to be scanned are annotated or specific locations on the slide to be scanned by the LSC are annotated in a fixed area centered on the annotation position. The positional frame of reference is translated back to that of the LSC. The LSC itself already provides the slide area and specific cell marking function by allowing annotation of corner positions or specific cells by the user, while the slide is on the stage of the LSC. Annotations may be made on an encoder as well as on the LSC.

In an embodiment wherein the X and Y axis movement of the microscope stage is motorized, the encoder can automatically relocate events of interest during the slide review process which had been electronically marked during the screening process. Efficient review is therefor possible in order to ease the heavy burden placed on cytopathologists. In particular, events to be reviewed can be keyed by the type of event, i.e., all positive events reviewed first followed by all atypicals, etc.

In addition to motorization, for familiarity of users with normal operation, the microscope stage may be also manually controllable through the standard stage motion mechanisms used in normal microscope operation, such as by means of a dual concentric shaft encoder. The dual encoder is mounted on the microscope and equipped with dual knob similar to those of a standard microscope. Motion of the outer knob and encoder generates pulses and the direction sense so that the motorized stage is made to move in the Y direction. Motion of the inner knob and encoder causes corresponding X motion of the microscope stage. Other devices such as a mouse or pointing tablet (Glidepoint®, Alps Electric, San Jose, Calif.) may be used to cause slide movement.

It is understood that the details of the above system and the various preferred embodiments are not to be construed as limitations of the present invention and that features and changes in the system may be made without departing from the scope of the present invention as set forth in the following claims.

We claim:

1. A method for network review of a specimen slide having a specimen and for network review of a manner of a prior microscope examination of the specimen slide with a microscope having a movable slide stage for mounting the specimen slide, the method comprising the steps of:

(a) operatively linking a means for computing, with a means for correlation movement sensing, to the movable slide stage, to correlatively record movement of the movable slide stage in an x-y direction plane in which the movable slide stage is movable;

(b) recording movements and locations of the movable slide stage during the prior microscope examination, at locations on the specimen slide, with the means for computing, pursuant to programmed instructions, into a means for data storage, wherein the means for computing, pursuant to additional programmed instructions automatically records, into the means for data storage at the recorded locations, predetermined indicia, with the predetermined indicia correlating to the microscope viewing area locations on the specimen slide, and wherein the predetermined indicia, correlating to viewing area locations of interest were marked and recorded with a distinguishing marking for subsequent review recognition to computer encode selected details of the specimen and the manner of the prior microscope examination;

(c) causing the means for data storage to be independently accessible by separate microscope stations in a network, each of the separate microscope stations comprising a microscope and a means for computer viewing, with each of the separate microscope stations being separately individually linked to at least one computer means for recalling the recorded movements, locations and predetermined indicia from the means for data storage for review on the computer viewing means;

(d) recalling, at one or more of the separate microscope stations, from the means for data storage, a computer generated image of a slide with the predetermined indicia thereon, onto the computer viewing means of the respective microscope station, for review of the manner in which a prior microscope examination of the specimen slide was conducted;

(e) placing the specimen slide on the movable slide stage of the microscope, at the respective microscope station, with the microscope thereat being further operatively linked with the means for computing, by correlation movement sensing means; and (f) moving the moveable slide stage, with concomitant specimen slide movement, with correlation of each subsequent microscope viewing area with indicia on the computer generated image, by means for indicating, whereby correlated indicia having a distinguishing marking thereon is directly viewable with the microscope.

2. A method for network review of a specimen slide having a specimen and for network review of a manner of a prior microscope examination of the specimen slide with a microscope having a movable slide stage for mounting the specimen slide, the method comprising the steps of:

(a) operatively linking a means for computing, with a means for correlation movement sensing, to the movable slide stage, to correlatively record movement of the movable slide stage in an x-y direction plane in which the movable slide stage is movable;

(b) recording movements and locations of the movable slide stage during the prior microscope examination, at locations on the specimen slide, with the means for computing, pursuant to programmed instructions, into a means for data storage, wherein the means for computing, pursuant to additional programmed instructions and a clock, automatically records, into the means for data storage, at the recorded locations on the specimen slide, predetermined indicia at predetermined time intervals, determined by the clock, with the predetermined indicia correlating to the microscope viewing area locations on the specimen slide, at the predetermined time intervals, and wherein the predetermined indicia, correlating to viewing area locations of interest were optionally marked and recorded with a distinguishing marking for subsequent review recognition to computer encode selected details of the specimen and the manner of the prior microscope examination;

(c) causing the means for data storage to be independently accessible by separate microscope stations in a network, each of the separate microscope stations comprising a microscope and a means for computer viewing, with each of the separate microscope stations being separately individually linked to at least one computer means for recalling recorded movements, locations and predetermined indicia from the means for data storage for review on the computer viewing means; and (d) recalling, at one or more of the separate microscope stations, from the means for data storage, a computer generated image of a slide with the predetermined indicia thereon, onto the computer viewing means of the respective microscope station, for review of the manner in which a prior microscope examination of the specimen slide was conducted, and if the predetermined indicia correlating to sites of interest have been marked with a distinguishing marking:

i) placing the specimen slide on the movable slide stage of the microscope, at the respective microscope station, with the microscope thereat being further operatively linked with the means for computing, by correlation movement sensing means; and ii) moving the moveable slide stage, with concomitant specimen slide movement, with correlation of each subsequent microscope viewing area with indicia on the computer generated image, by a means for indicating, whereby correlated indicia having a distinguishing marking thereon are directly viewable with the microscope.

3. A method for network review of a specimen slide having a specimen and for network review of a manner of a prior microscope examination of the specimen slide with a microscope having a movable slide stage for mounting the specimen slide, the method comprising the steps of:

(a) operatively linking a means for computing, with a means for correlation movement sensing, to the movable slide stage, to correlatively record movement of the movable slide stage in an x-y direction plane in which the movable slide stage is movable;

(b) recording movements and location information of the movable slide stage during the prior microscope examination, with the means for computing, pursuant to programmed instructions, into a means for data storage, wherein the means for computing, pursuant to additional programmed instructions and a clock, automatically records, into the means for data storage, predetermined indicia at predetermined time intervals, determined by the clock, with the predetermined indicia correlating to the microscope viewing area locations on the specimen slide, at the predetermined time intervals, and wherein the predetermined indicia, correlating to viewing area locations of interest were optionally marked and recorded with a distinguishing marking for subsequent review recognition to computer encode selected details of the specimen and the manner of the prior microscope examination;

(c) causing the means for data storage to be independently accessible by separate microscope stations in a network, each of the separate microscope stations having a microscope and means for computing;

(d) linking each one of the microscope stations to at least one means for computing capable of recalling the recorded movements and the recorded location information from the means for data storage; and (e) reviewing the specimen slide at a location remote from the microscope used in the prior microscope examination.

4. The method of claim 3, wherein the location information further comprises grayscale display information, which indicates by shades of increasingly darker shades of gray increasing dwell time during the prior microscope examination, degree of overlap of viewing areas and proximity to a center of a viewing area, whereby a degree of efficacy of the prior microscope examination may be determined at a remote location.

5. The method of claim 3, wherein the separate microscope stations are further independently linked to a hospital HIS system whereby means for computer viewing are made to provide simultaneous slide analysis review in relation to a medical history of a patient from whom the specimen was derived.

6. The method of claim 3, wherein areas on the specimen slide, selected for additional review during the prior microscope examination, are video digitized areas representative in appearance of the areas on the specimen slide.

7. The method of claim 6, wherein the separate microscope stations are further independently linked to a library data base of known slide specimen images whereby the video digitized areas are visually compared to known slide specimens in a side by side comparison.

8. The method of claim 6, wherein the separate microscope stations are further independently linked to a cell analysis instrument, whereby cell analysis of other specimens from the same source as the specimen of the prior microscope examination, is effected by the cell analysis instrument and wherein analysis data from the cell analysis instrument and results of the prior microscope examination are simultaneously available at the separate microscope stations, for review thereof.

9. The method of claim 8, wherein the cell analysis instrument is a hematology analyzer.

10. The method of claim 8, wherein the cell analysis instrument is a Pap smear analyzer.

11. The method of claim 8, wherein the cell analysis instrument is an image analyzer.

12. The method of claim 8, wherein the cell analysis instrument is a laser scanning cytometer.

13. The method of claim 3, wherein the separate microscope stations each have microscopes with motor driven stages, with computer control, to re-scan slides or slide images only at viewing area locations of interest which were marked and recorded with a distinguishing marking.

14. The method of claim 8, wherein at least one of the separate microscope stations provide at least one of anatomic pathology and cytology diagnosis reports to a central Hospital Information System, where a permanent record thereof is generated.

15. The method of claim 3, wherein during the prior microscope examination, multiple images of selected fields, at different focuses of the microscope and at any magnification are stored and indexed, and wherein microscopes at the microscope stations are equipped with means for automatically moving a focus position as images are being captured, stored, and recalled.

16. A network of interconnected microscope stations comprising:

(a) a means for operatively linking microscope stations; and (b) a plurality of microscope stations connected to the means for operatively linking microscope stations, wherein a microscope of the plurality of microscope stations includes:

(i) a movable slide stage for mounting a specimen slide having a specimen;

(ii) a means for computing wherein information relating to the specimen slide being examined by the microscope is stored by the means for computing and is made accessible to other microscopes; and (iii) means for automatically recording location information of interest of the movable slide stage during a microscope examination, wherein the automatically recorded location information of interest represents microscope viewing locations on the specimen slide that are locations of interest.

17. The network of claim 16, wherein each microscope station in the network of the interconnected microscope stations further comprises a terminal for a data base having information relevant to appropriate examination of the slide specimen.

18. The network of claim 17, wherein the data base comprises a Hospital Information System and wherein the slide specimen is from a patient whose medical records are contained in a Hospital Information System.

19. The network of claim 18, wherein selected areas of the slide specimen are converted to video digitized images by means for conversion and means for storing a data base, with the video digitized images being accessible at the interconnected microscope stations and wherein the data base further includes a library data base of known slide specimen images whereby the video digitized images are visually compared to known slide specimens in a side by side comparison on a means for video display at any of the interconnected microscope stations.

20. The network of claim 18, wherein each interconnected microscope station of the network of interconnected microscope stations further comprises means for generating a report into the Hospital Information System for a patient, based on a slide specimen examination.

21. The network of claim 16, wherein the network further includes at least one cell analysis instrument and wherein at least one interconnected microscope station of the network of interconnected microscope stations further comprises a terminal for receipt of analysis from the cell analysis instrument.

22. The apparatus of claim 16 further comprising a means for recording time information of the movable slide stage during a prior microscope examination, wherein the time information includes an amount of time spent on viewing a location of interest.

23. The apparatus of claim 22 further comprising a means for encoding selected details of the specimen and a manner of the microscope examination based on the location information and the time information.

24. The apparatus of claim 16, wherein separate microscope stations are further independently linked to a cell analysis instrument, whereby cell analysis of other specimens from the same source as the specimen of the microscope examination, is effected by the cell analysis instrument and wherein analysis data from the cell analysis instrument and results of the microscope examination are simultaneously available at the separate microscope stations, for review thereof.

25. The apparatus of claim 24, wherein the cell analysis instrument is a hematology analyzer.

26. The apparatus of claim 24, wherein the cell analysis instrument is a Pap smear analyzer.

27. The apparatus of claim 24, wherein the cell analysis instrument is an image analyzer.

28. The apparatus of claim 24, wherein the cell analysis instrument is a laser scanning cytometer.

* * * * *